US00PP32805P3

(12) United States Plant Patent
Chandra et al.

(10) Patent No.: US PP32,805 P3
(45) Date of Patent: Feb. 9, 2021

(54) ZOYSIAGRASS NAMED 'DALZ 1308'

(50) Latin Name: ***Zoysia minima* x *Zoysia matrella* $F_1$ hybrid**
Varietal Denomination: DALZ 1308

(71) Applicant: The Texas A&M University System, College Station, TX (US)

(72) Inventors: Ambika Chandra, Dallas, TX (US); Anthony D. Genovesi, Dallas, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 16/501,556

(22) Filed: Apr. 29, 2019

(65) Prior Publication Data

US 2020/0344933 P1 Oct. 29, 2020

(51) Int. Cl.
*A01H 5/12* (2018.01)
*A01H 6/46* (2018.01)

(52) U.S. Cl.
USPC ..... Plt./390
CPC ..... *A01H 6/469* (2018.05)

(58) Field of Classification Search
USPC ..... Plt./390
CPC ..... A01H 6/469
See application file for complete search history.

(56) References Cited

U.S. PATENT DOCUMENTS

| | | | |
|---|---|---|---|
| PP10,636 | P | 10/1998 | Engelke |
| PP11,515 | P | 9/2000 | Engelke |
| PP14,130 | P2 | 9/2003 | Engelke et al. |
| PP25,203 | P3 | 12/2014 | Doguet et al. |
| 2014/0310842 | P1 | 12/2014 | Doguet et al. |

OTHER PUBLICATIONS

"Texas A&M Agrilife Research licenses DALZ 1308 for production", Gabe Saldana, https://soilcrop.tamu.edu/dalz1308-licensed-for-production/ Jan. 24, 2018, downloaded on Feb. 28, 2020.*
Anderson, Taxonomy of *Zoysia* (Poaceae) morphological and molecular variation (book), Ph.D. diss., Texas A&M University, College Station, Texas 2000.
Atkinson, "Response of warm season turfgrasses to reduced light environments," M.S. thesis, Clemson University, Clemson, S.C., 2010.
Baldwin, et al., "Impacts of Altered Light Spectral Quality on Warm-season Turfgrass Growth under Greenhouse Conditions," Crop Science 49(4):1444-1453, 2009.
Briscoe, et al. "Evaluation of 'Miniverde' Bermudagrass and 'Diamond' Zoysiagrass Putting Green Establishment using Granular Fertilizer Applications," Horticultural Science 47(7):943-947, 2012.
Brosnan, et al., "Zoysiagrass Seedhead Suppression with Imidazolinone Herbicides," Weed Technology 26 (4):708-713, 2012.
Bunnell, et al., "'TifEagle' Bermudagrass Response to Growth Factors and Mowing Height when Grown at Various Hours of Sunlight," Crop Science 45(2):575-581, 2005.
Duich and Langlois, "Management factors affecting green speed," The 56th International Golf Course Conference and Show. Washington, D.C., Penn State pp. 3&5, 1985.
Engelke, et al., "Registration of 'Diamond' Zoysiagrass," Crop Science 42(1):304-305, 2002.
Forbes and Ferguson, "Observations on the *Zoysia* grasses," Greenkeepers Rep. 15:7-9, 1947.
Fry and Huang, Applied Turfgrass Science and Physiology (book), Wiley, Hoboken, NJ, 2004.
Genovesi, et al., "Development of Cold-hardy Cultivars of Zoysiagrass for Golf Courses in the Transition Zone," USGA Turfgrass Environ. Res. Summ. (in-press), pp. 52-55, 2018.
Hinton, "Differences in Establishment Rate, Freeze Tolerance, and Response to nitrogen fertility rate and mowing height on nine cultivars of zoysiagrass," M.S. thesis, North Carolina State Univ., Raleigh, NC, 2011.
Karcher and Richardson, "Batch Analysis of Digital Images to Evaluate Turfgrass Characteristics," Crop Science, 45(4):1536-1539, 2005.
Kauffman, "Investigating Cold Hardiness and Management Practices of Warm-season Putting Green Species in the Transition Zone," Ph.D. diss., Univ. of Tennessee, Knoxville, TN, 2010.
Kauffman, et al., "Field Sampling Warm-season Putting Greens for Thatch-mat Depth and Organic Matter Content," HortTechnol. 23(3):369-375, 2013.
Loch, "Zoysiagrass: An overview of taxonomy, morphology, genetic variation and environmental adaptation in relation to turf management and use," In: Proceedings of the 2015 International Zoysiagrass Symposium, Okinawa, Japan. Nov. 22 p. 30-47, Tokyo: Japanese Society of Turfgrass Science, 2015.
Marcum and Murdoch, "Growth Responses, Ion Relations, and Osmotic Adaptations of Eleven C4 Turfgrass to Salinity," Agronomy J, 82(5):892-896, 1989.
McCullough, et al., "Seedhead Development of Three Warm-season Turfgrasses as Influenced by Growing Degree Days, Photoperiod, and Maintenance Regimens," Int. Turfgrass Soc. Res. J., 13(1):321-329, 2017.
Morris, "NTEP evaluates cool/warm season grass experiments," Turfgrass Producers of Texas, The Pallet Newsletter, 2017.
New Zealand Plant Conservation Network, "*Zoysia minima*," http://www.nzpcn.org/nz/c/flora/factsheets/NZPCN_Species_1372.pdf (accessed Mar. 20, 2017), Jan. 20, 2014.
Patton, "Selecting Zoysiagrass Cultivers: Turfgrass Quality, Growth, Pest and Environmental Stress Tolerance," Appl. Turfgrass Sci., 2009.

(Continued)

*Primary Examiner* — Anne Marie Grunberg
(74) *Attorney, Agent, or Firm* — Dentons US LLP

(57) ABSTRACT

'DALZ 1308' is a new and distinct *Zoysia minima* x *Zoysia matrella* $F_1$ hybrid variety with novel characteristics that included a dwarf canopy height, high shoot density, fine leaf texture, medium green genetic color in summer, extended fall and winter color retention, good turf quality, and resistance to tawny mole cricket (*Neoscapteriscus vicinus*) damage.

4 Drawing Sheets

(56) References Cited

OTHER PUBLICATIONS

Patton and Reicher, "Zoysiagrass Species and Genotypes Differ in Their Winter Injury and Freeze Tolerance," Crop. Sci. 47(4):1619-1627, 2007.
Patton, et al., "Fall Applications of Proxy (Ethephon) Suppress Spring Seedheads of 'Meyer' Zoysiagrass," Crop Forage Turfgrass Mgmt. 4(1):180012, 2018.
Patton, et al., "Stolon Growth and Dry Matter Partitioning Explain Differences in Zoysiagrass Establishment Rates," Crop Sci., 47(3):1237-1245, 2007.
Patton, et al., "Zoysiagrass Growth as Influenced by Nitrogen Source in a Greenhouse Trial," Ark. Turfgrass Rep. 2009, Ark. Agric. Exp. Stn. Res. Ser. 579:74-76, 2010.
Patton, et al., "Zoysiagrass (*Zoysia* spp.) History, Utilization, and Improvement in the United States: A Review," Crop Sci. 57(Supp. 1):S-37-S-72, 2017.
Qian and Engelke, "'Diamond' Zoysiagrass as Affected by Light Intensity," J. Turfgrass Mgmt. 3(2):1-13, 1999.
Qian, et al., "Salinity Effects on Zoysiagrass Cultivars and Experimental Lines," Crop Sci. 40(2):488-492, 2000.
Richardson, et al., "Winterkill in the 2007 Arkansas Zoysiagrass Trial," Ark. Turfgrass Rep. 2010, Ark. Agric. Exp. Stn. Res. Ser. 593:26-29, 2012.
Riffel, et al., "Performance of three warm-season turfgrasses cultured in shade: Zoysiagrass," Texas Turfgrass Res. Rep. 95-1. Texas Agric. Exp. Stn., Dallas, TX. p. 60-65,1995.
Sladek, et al., "Effect of Genotype, Planting Date, and Spacing on Zoysiagrass Establishment from Vegetative Plugs," HortScience 46(8):1194-1197, 2011.
Sladek, et al., "Evaluation of Zoysiagrass Genotypes for Shade Tolerance," HortScience 44(5):1447-1451, 2009.
Stiglbauer, et al., "'Diamond' Zoysiagrass Putting Green Establishment Affected by Sprigging Rates, Nitrogen Sources, and Rates in the Southern Transition Zone," HortScience 44(6):1757-1761, 2009.
Tegg and Lane, "A comparison of the performance and growth of a range of turfgrass species under shade," Aust. J. Exp. Agric. 44(3):353-358, 2004.
Thomas, "Equipment extra: Eddie Stimpson's slant on putting," Golf Digest, Oct. 2001.
Throssell, "Management Factors Affecting Putting Green Speed," M.S. Thesis. Penn. State Univ., State College, PA, 1981.
Tsuruta, et al., "*Zoysia*," In: C. Kole, editor, Wild crop relatives: Genomic and breeding resources (book), Millets and Grasses, Springer-Verlag,Berlin & Heidelberg: p. 297-309, 2011.
Uddin, et al., "Relative salinity tolerance of Warm season turfgrass species," J. Environ. Biol. 32(3):309-312, 2011.
Wherley, et al., "Low-input Performance of Zoysiagrass (*Zoysia* spp.) Cultivars Maintained under Dense Tree Shade," HortScience 46(7):1033-1037, 2011.
Woods, "Why manilagrass (*Zoysia matrella*) is the best choice for links-style golfing surfaces in East and Southeast Asia," Asian Turfgrass Center, Bangkok, Thailand, www.asianturfgrass.com, 2013.
Yaneshita, et al., "Genetic variation and interspecific hybridization among natural populations of zoysiagrasses detected by RFLP analyses of chloroplast and nuclear DNA," Genes Genet. Syst. 72(4):173-179, 1997.

* cited by examiner

ZOYSIAGRASS NAMED 'DALZ 1308'

Latin name of the genus and species of the plant claimed: *Zoysia minima* x *Zoysia matrella* $F_1$ hybrid.

Variety denomination: 'DALZ 1308'.

BACKGROUND OF THE INVENTION

The *Zoysia* genus is indigenous to Pacific Rim countries with a geographic distribution extending from 42° N to 42° S, and displays a wide range of genetic variability that includes 11 different species. Most zoysiagrasses are tetraploid (2n=4x=40); however, there are diploid *Z. matrella* (L.) Men. accessions (2n=2x=20). The species within the *Zoysia* genus are cross compatible, which makes interspecific hybridization feasible. *Zoysia* spp. possess good tolerance to heat, shade, and salt, and require minimal nutrition and mowing. Some zoysiagrass cultivars, particularly within *Z. japonica*, also exhibit good freezing tolerance.

The following *Zoysia* species are recognized as turfgrasses in the U.S.: *Z. japonica* Steud. (Japanese lawngrass), *Z. matrella* (L.) Merr. (Manilagrass), and *Z. pacifica* (Goudsw.) M. Hotta and Kuroki (Mascarenegrass). Zoysiagrass is best adapted and widely used in the southern and southeastern regions of the U.S., and limited freezing tolerance is the primary factor hindering widespread implementation of zoysiagrass in other regions, including the region referred to as the "transition zone," which extends through the central portion of the United States from the Atlantic Coast to eastern New Mexico.

Ultradwarf bermudagrass (*Cynodon* spp.) cultivars are most widely used for golf course putting greens in the southern U.S. as they exhibit faster establishment rates and produce quality putting surfaces, but in comparison to zoysiagrass they exhibit limited tolerance to cold, salinity, and shade. Zoysiagrass are one of the most versatile warm-season turfgrasses and is used on lawns, landscapes, and golf courses; however, their utility on golf course putting greens has been limited.

*Z. matrella* is a finer-textured zoysiagrass species that generally displays a higher turfgrass quality, and a tolerance to low mowing heights, shade, and salinity. The *Z. matrella* (L.) Men cultivar 'Diamond' (U.S. Plant Pat. No. 10,636) was one of the finest-textured zoysiagrass at the time of its release, and has since been used for fairways, tees, and putting greens in the south and southeastern U.S. 'Diamond' has low fertility requirements and tolerance to shade and salinity; however, relatively slow ball roll, sensitivity to winterkill, and high seedhead production have posed challenges to its widespread use on putting greens. Another *Z. matrella* (L.) Merr cultivar, 'L1F' (U.S. Plant Pat. No. 25,203), exhibits reduced seedhead production when compared against 'Diamond', but is more sensitive to both winterkill and large patch disease. While both 'Diamond' and 'L1F' exhibit the fine leaf texture that is associated with *Zoysia matrella* (L.) Merr cultivars as compared to other commercially available zoysiagrass cultivars, they do not tolerate low mowing heights, do not produce desirable ball roll, and are not sufficiently tolerant to the relevant environmental stresses.

Another species of zoysiagrass is *Z. minima* (Colenso) Zotov, which is one of three species native to New Zealand. *Z. minima* is a creeping perennial with "diminutive" stature that produces a single raceme per spike with less than three spikelets, and a threadlike leaf blade. The natural habitat for

*Z. minima* is in sandy or well-drained soils along coastlines and up to elevations of 600 m.

SUMMARY OF THE INVENTION

The present disclosure relates to a new and distinct interspecific $F_1$ hybrid variety of zoysiagrass named 'DALZ 1308'. 'DALZ 1308', formerly tested as TAES 5458-10, was produced in 2004 near Dallas, Tex. by controlled hand-pollination between TAES 5194-5, a *Z. minima* (Colenso) Zotov ecotype (unpatented), (female parent) and the cultivar 'Diamond' (male parent). Progeny produced by this cross were selected for advancement during trials conducted near Gainesville, Fla. from 2006 to 2008 and 2013 to 2015 and in Dallas, Tex. from 2009 to 2012 and 2014 to 2018. 'DALZ 1308' was also selected for advancement and inclusion in the 2013 National Warm-Season Putting Grass Trial conducted by the National Turfgrass Evaluation Program (NTEP). 'DALZ 1308' was first asexually propagated in Dallas, Tex. via sprigs.

'DALZ 1308' differs from its parents and all other known zoysiagrass cultivars. The following are the most outstanding and distinguishing characteristics of 'DALZ 1308': (1) it exhibits increased ball roll distance; (2) it exhibits increased resistance to winter injury; (3) it exhibits finer leaf texture; (4) it exhibits an increased establishment rate; and (5) it exhibits acceptable quality and a slower growth rate under moderate (60%) shade levels. 'DALZ 1308' turf can also be distinguished at least based upon its dwarf canopy height, high shoot density, fall and winter color retention, good turf quality, and resistance to tawny mole cricket (*Neoscapteriscus vicinus*) damage.

'DALZ 1308' turf can be distinguished from TAES 5194-5 turf (female parent) at least based upon seedhead spikelet number and cold hardiness. 'DALZ 1308' turf can be distinguished from 'Diamond' turf (male parent) at least based upon canopy height. 'DALZ 1308' turf exhibits 1 seedhead spikelet, whereas TAES 5194-5 turf exhibits 3 seedhead spikelets. 'DALZ 1308' exhibits increased cold hardiness compared to TAES 5194-5. 'DALZ 1308' turf exhibits an average canopy height of 0.9 cm; whereas, 'Diamond' turf exhibits an average canopy height of 1.7 cm.

BRIEF DESCRIPTION OF THE DRAWINGS

'DALZ 1308' is illustrated by the accompanying photographs, which show the turf's leaf texture, shoot density, inflorescences, canopy height, ligule hairs, and percent establishment. The colors shown are as true as can be reasonably obtained by conventional photographic procedures.

DETAILED BOTANICAL DESCRIPTION

The following detailed description sets forth the distinctive characteristics of 'DALZ 1308'. Color references are to the Munsell Color Charts for Plant Tissues, 1977 Edition, unless otherwise indicated. Color designations provided refer to both mature and immature stages unless otherwise indicated. If any Munsell color designations below differ from the accompanying photographs, the Munsell color designations are accurate.

Plant:

*Growth habit.*—Prostrate.

*Natural plant height (prior to stem elongation).*—0.9 cm.

*Tillers on the culm.*—Absent.

*Self-fertility.*—Poor fertility, with occasional outcrossing.

Rhizomes:

1st *internode length.*—9.8 mm.

2nd *internode length.*—11.5 mm.

3rd *internode length.*—11.2 mm.

4th *internode length.*—11.5 mm.

4th *internode diameter.*—1.0 mm.

4th *node diameter.*—1.5 mm.

Leaves:

*Length.*—7.93 mm.

*Width.*—0.725 mm.

*Leaf curling.*—Blade rolled in the bud.

*Leaf sheath pubescence.*—Absent.

*Leaf sheath color.*—7.5 GY 8/2.

*Leaf collar color.*—2.5G 9/2.

*Anthocyanin coloration of the basal leaf sheath.*—None.

*Lower surface leaf coloration.*—5GY 5/4.

*Upper surface leaf coloration.*—5GY 5/4.

*Auricles.*—Absent.

*Ligules.*—Hairy.

*Leaf blade venation pattern.*—Parallel.

Stem color: 7.5GY 7/6.

Stolon nodes and internodes: Anthocyanin 5R 3/4.

Shoots: 5GY 4/8.

Ascending culm internode length: 7.49 mm.

Culm node pubescence: Absent.

Time of flowering: April to May (in Dallas, Tex.).

Glumes: Absent.

Lemmas: Present.

Lemma shape: Half of an elliptic.

Lemma length: 2.58 mm.

Lemma colors: Light green when immature (2.5GY 8/10) with anthocyanin (5RP 7/6), tan when mature (2.5GY 8/2).

Palea shape: Half of an elliptic.

Palea size: 2.58 mm.

Palea colors: Light green when immature (2.5GY 8/10) with anthocyanin (5RP 7/6), tan when mature (2.5GY 8/2).

Bristles: Absent.

Ligule color: 2.5G 9/2.

Inflorescence:

*Type.*—Raceme spike with sessile flowers.

*Shape of rachis.*—Cylindrical.

*Collar of the rachis.*—Open.

*Panicle description.*—Raceme spike with sessile flowers.

*Panicle length.*—5.75 mm.

*Panicle diameter.*—0.936 mm.

*Color.*—5GY 7/6, anthocyanin 5RP 6/6.

*Stigma length.*—1.73 mm.

*Stigma color.*—2.5R 9/2.

*Stigma characterization.*—Translucent.

*Peduncle length.*—15.15 mm.

*Pedicel.*—Fused to the rachis.

*Pedicel color.*—Not visible (fused to the rachis).

Awns: Absent.

Culm diameter: 0.31 mm.

Number of panicle bearing tillers in the culm: 1.

Culm color: 7.5GY 5/4, anthocyanin base 5RP 7/6.

Culm anthocyanin coloration of the nodes and internodes: No anthocyanin coloration.

Caryopsis shape: Elliptic.

Grain shape: Elliptic.

Florets per spike: Mean of one.

Morphological Analysis of 'DALZ 1308'

Figure 1:
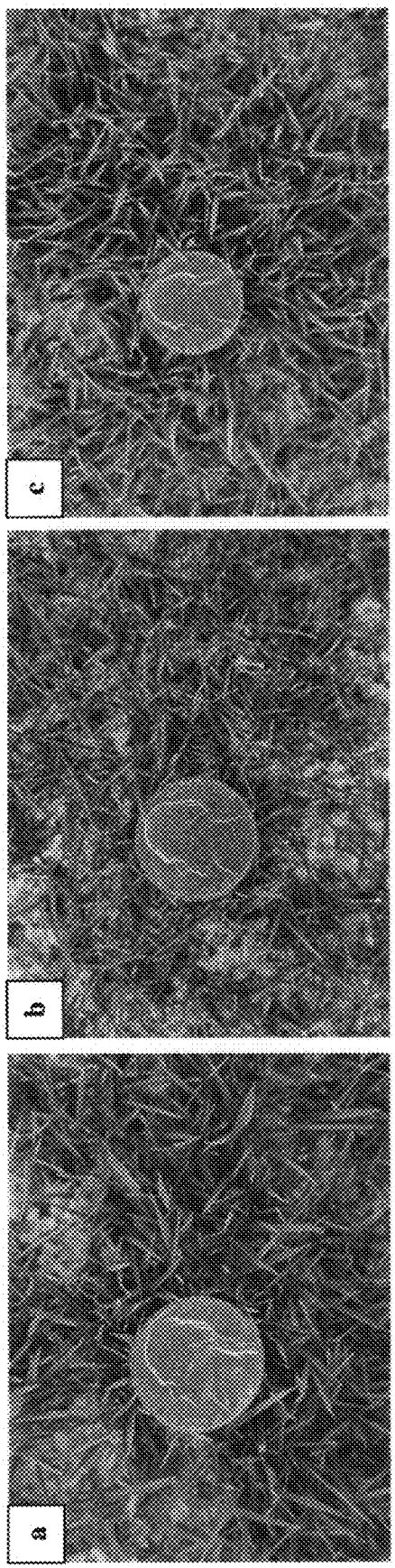
FIG. 1—Shows the leaf texture and shoot density of 'Diamond' (a), 'DALZ 1308' (b), and 'L1F' (c).
Figure 2:
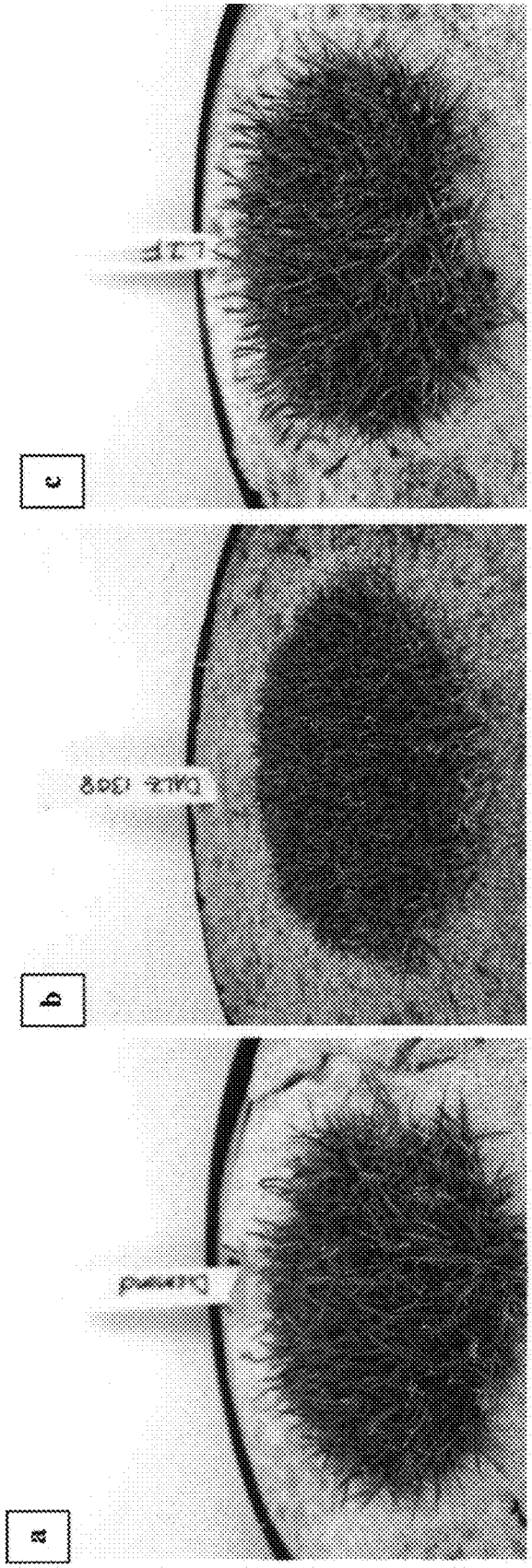
FIG. 2—Shows the inflorescences and canopy height of 'Diamond' (a), 'DALZ 1308' (b), and 'L1F' (c).
Figure 3:
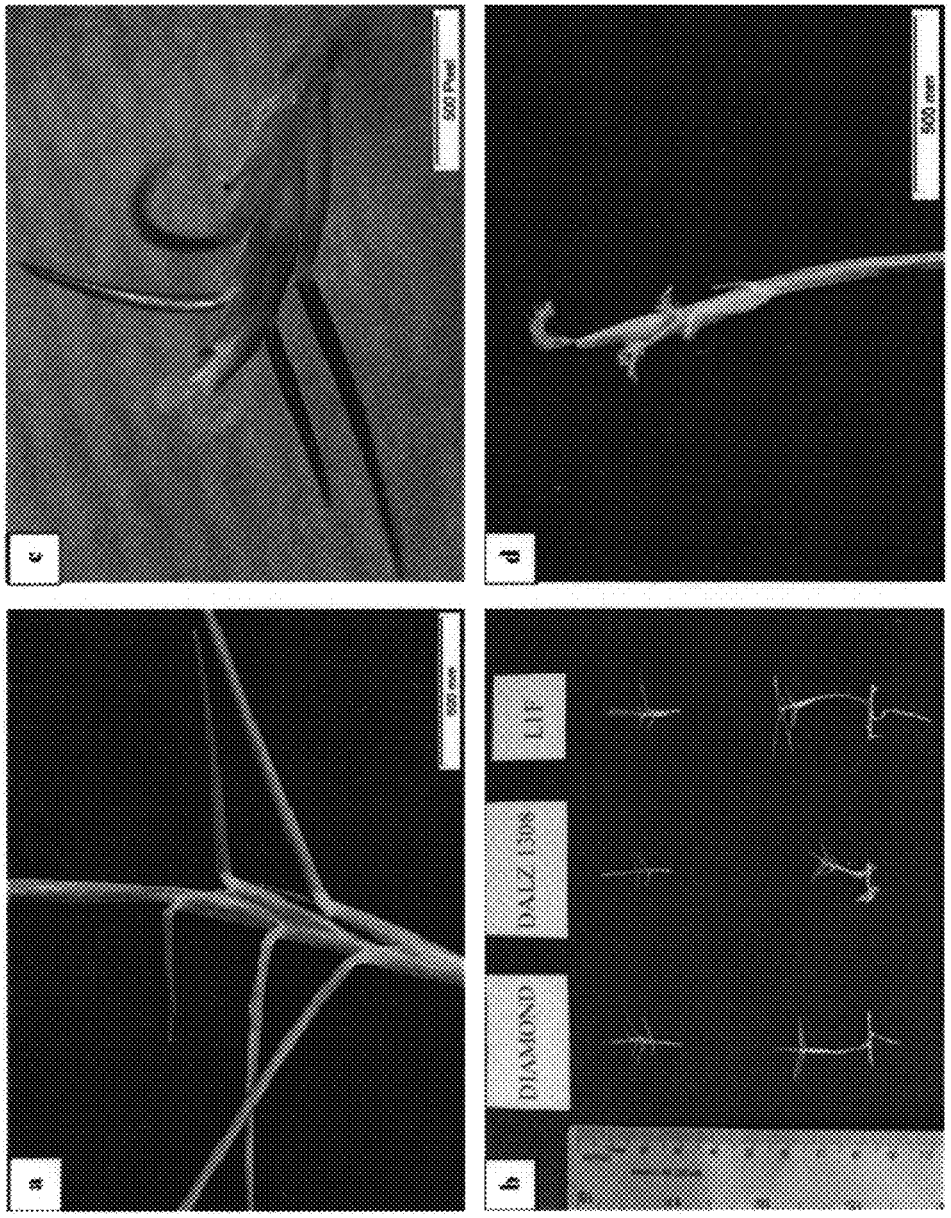
FIG. 3—Shows 'DALZ 1308' ligule hairs (a); the inflorescences and growth habit of 'Diamond', 'DALZ 1308', and 'L1F' (b); TAES 5194-5 inflorescences (c); and 'DALZ 1308' inflorescences (d).

'DALZ 1308' was morphologically compared to 'Diamond' and 'L1F' (Table 1; FIGS. 1-3). Plants were planted from sprigs on Jul. 22, 2015 in a sand-based putting green built to United States Golf Association (USGA) standards. Plots were 0.9 m×2.4 m and arranged in a randomized complete block design with four replications. Each plot received between 0.3 cm and 0.5 cm of topdressing sand monthly between April and September and were mowed every two weeks during the first 2 years of establishment to a height of 0.65 cm and to a height of 0.32 cm thereafter. Nitrogen (46-0-0 urea) was applied at a rate of 9.9 kg/ha per growing month during the first two years. Annual weeds were prevented with Oxadiazon once every spring and fall at a rate of 484.17 kg/ha. On Apr. 27, 2017, a total of four 10.2 cm diameter plugs were removed using a cup cutter to a depth of 15.2 cm from the established plots for each entry and were then potted in individual 7.6 L plastic pots filled with topdressing sand that were maintained under field conditions. Oxadiazon was applied as a pre-emergent at 484.17 kg/ha and during the first 8 weeks of establishment fertilizer (18-24-12) was applied every two weeks at a rate of 24.4 kg N/ha. Pots were maintained by hand trimming at a height of 0.318 cm after Jun. 2, 2017. Leaf length was measured between the base and tip of the third youngest fully extended and untrimmed leaves; leaf width was measured at the widest point above the collar of the third youngest leaves; internode length was measured between each of the youngest 5 nodes on 12 rhizomes; internode and node diameters were measured from the fourth youngest internode and node of 12 rhizomes; and canopy height was measured during one event from nine untrimmed leaves seven days after trimming. Inflorescence and seedhead traits, including stigma and anther color, were collected on Jun. 2, 2017. However, the 'DALZ 1308' turf lacked inflorescences at that time, and thus no comparison was made to the 'Diamond' and 'L1F' turfs that were both in flush. The Munsell Color Charts for Plant Tissues were used to determine color of adaxial leaf tissue, the fourth youngest internode, stigma, and mature anthers.

Morphological Comparison of 'DALZ 1308' to Commercial Varieties

Rhizome:

*Internode lengths.*—Those of 'DALZ 1308' were similar to those of 'Diamond' and shorter than those of 'L1F' (Table 1).

*Internode diameter.*—That of 'DALZ 1308' was similar to that of 'Diamond' and narrower than that of 'L1F' (Table 1).

*Node diameter.*—That of 'DALZ 1308' was similar to that of 'Diamond' and narrower than that of 'L1F' (Table 1).

Leaf blade:

*Length*.—That of 'DALZ 1308' was shorter than that of 'Diamond' and 'L1F' (Table 1).

*Width*.—That of 'DALZ 1308' was narrower than that of 'Diamond' and 'L1F' (Table 1).

Canopy height: That of 'DALZ 1308' was shorter than that of 'Diamond' and similar to that of 'L1F'.

TABLE 1

Morphological comparison of 'DALZ 1308' and commercial zoysiagrass cultivars.

| | Rhizome† | | | |
|---|---|---|---|---|
| | Internode Length | | | |
| Entry | 1st | 2nd | 3rd | 4th |
| | mm | | | |
| 'DALZ 1308' | 9.8 b | 11.5 b | 11.2 b | 11.5 b |
| 'Diamond' | 8.0 b | 9.2 c | 9.9 b | 10.7 b |
| 'L1F' | 13.8 a | 14.1 a | 14.3 a | 14.7 a |
| LSD¶ | 2.0 | 1.6 | 2.0 | 2.2 |

| | Rhizome† | | | | |
|---|---|---|---|---|---|
| | Internode | Node | Leaf Blade‡ | | |
| Entry | Diameter 4th | Diameter 4th | Length 3rd | Width 3rd | Canopy Height § (cm) |
| | mm | | | | |
| 'DALZ 1308' | 1.0 b | 1.5 b | 7.9 c | 0.7 b | 0.9 b |
| 'Diamond' | 1.1 ab | 1.6 ab | 13.6 a | 1.5 a | 1.7 a |
| 'L1F' | 1.2 a | 1.8 a | 11.9 b | 1.4 a | 1.1 b |
| LSD¶ | 0.2 | 0.2 | 1.4 | 0.1 | 0.2 |

†Means in each column were calculated from twelve measurements collected on 15 Sep. 2017. Internode length was measured from the first, second, third, and fourth youngest internodes. Internode and node diameters were measured from the fourth youngest internode and node.
‡Means for leaf blade length and width were calculated from twelve measurements of the third youngest leaf blades on 2 Jun. 2017.
§Canopy height was measured seven days after trimming on 15 Sep. 2017 from a total of nine measurements for each cultivar.
Cultivars followed by the same letter in each column are not significantly different by Fisher's protected LSD ($P > 0.05$).

Establishment and Turfgrass Quality Evaluation

Vegetative plugs of 88 experimental zoysiagrass entries, including 'DALZ 1308', and 'Diamond', were planted in a randomized complete block design on a USGA grade putting green in 2006 in Gainesville, Fla. Turfgrass quality, genetic color, shoot density, spring greenup, seedhead density, and resistance to mole crickets were visually rated on a "1" to "9" scale from 2006 to 2008 (Table 2).

Vegetative plugs of 6 elite selected entries, including 'DALZ 1308' and the commercial cultivar 'Diamond', were planted in a randomized complete block design on a USGA grade putting green on Jun. 24, 2013 in Gainesville, Fla. The study included three replications in a randomized complete block design. Percent green cover was visually rated once in April and May of 2014. Turfgrass quality was visually rated monthly on a "1" to "9" scale throughout 2014, 2015, and 2016. 'DALZ 1308' exhibited an increased shoot density and seedhead density when compared to 'Diamond'. 'DALZ 1308' and 'Diamond' exhibited similar turfgrass quality, spring greenup, tawny mole cricket resistance, and percent establishment (Table 2).

Multi-State Progeny Evaluation 10 elite experimental zoysiagrass entries, including 'DALZ 1308' and 'Diamond', were evaluated across 10 locations representing USDA cold hardiness zones 6a to 9b (Tucson, Ariz.; Rancho Mirage, Calif.; Jay, Fla.; Griffin, Ga.; Starkville, Miss.; College Station, Tex.; Fayetteville, Ariz.; Lexington, Ky.; Richmond, Va.; and Bloomington, Ind.) from 2013 through 2017. Plots were established from vegetative plugs in either sand (CA, GA, KY, MS), sandy loam (IN), or silty clay loam (VA) soil textures. Plots were covered with protective fabric during the winter months of 2013, 2014, and 2015 in AR, IN, MS, and VA, and only in 2013 in KY.

Fertility treatments varied by location. Most locations followed minimal management, applying up to 14.7 kg $N/m^2$/year, but both AK and CA applied between 24.4 kg and 34.2 kg $N/m^2$/year. Irrigation was supplied to prevent stress, except in VA where irrigation was only supplied to prevent dormancy. In the first year of establishment, mowing heights were set to 1.3 cm, except in VA where the height was set to between 1.5 cm to 2.5 cm. From 2015 through 2017, the mowing heights were adjusted to between 0.36 cm and 0.42 cm.

Visual traits that were evaluated on a percentage basis included establishment and winterkill. Qualitative traits that were rated on a "1" to "9" scale included turfgrass quality (low to high), leaf texture (extremely coarse to very fine), shoot density (bare to very dense), genetic color (light green to dark green), fall/winter color (straw brown or no color to dark green), spring greenup (straw brown to completely dark green), and seedheads (heavy density to no seedheads) (Tables 3-7). All traits were rated according to evaluation guidelines defined by NTEP. Frequency of data collection for each trait varied by location, and is described in the respective table footnotes. Data were analyzed using JMP® 10 software. Cultivar means were separated using Fisher's protected LSD ($P \leq 0.05$). Green speeds (ball roll distances) were measured with a stimpmeter (Table 8). Analysis of variance for ball roll indicated that no significant differences were observed between the ratings taken the day of and a day after mowing, and therefore that data was pooled.

Vegetative plugs of 40 experimental fine-textured zoysiagrass lines, including 'DALZ 1308' and cultivars 'Diamond' and 'L1F', were planted as 72 plugs in each of 1.8 m×2.4 m plots replicated three times on a USGA grade putting green with a 100% sand base in Dallas, Tex. Oxadiazon was applied at planting and once during the spring and fall between 112.1 kg/ha and 224.2 kg/ha to prevent emergence of annual weeds. Nitrogen was applied monthly during the growing season to reach a rate of 146.5 kg/ha. The putting green was heavily top-dressed in the first full year of establishment, and lightly top-dressed during the growing season from 2016 to 2017. The putting green was covered with a polypropylene cloth for winter protection from 2014 to 2015 and Nov. 20, 2015 through Mar. 2, 2016. Mowing commenced on Jul. 21, 2015 (320 days after planting) at a height of 1.3 cm monthly, followed once every two weeks by a height of 0.6 cm on Nov. 20, 2015 until Jul. 7, 2016 when mowing began weekly. A mowing height of 0.3 cm began Mar. 20, 2017 twice weekly and three times weekly starting Jun. 7, 2017. Irrigation was supplied as needed to promote establishment and prevent freezing damage and summer stress. Performance traits such as establishment, turfgrass quality, texture, genetic color, shoot density, fall color, and spring greenup were rated according to NTEP guidelines. Percent seedhead cover was visually rated from 1 to 100% in the spring, summer, and fall (Tables 9-10). Green speeds (ball roll distances) were measured with a stimpmeter (Table 8).

Shade Level Evaluation

Figure 4:
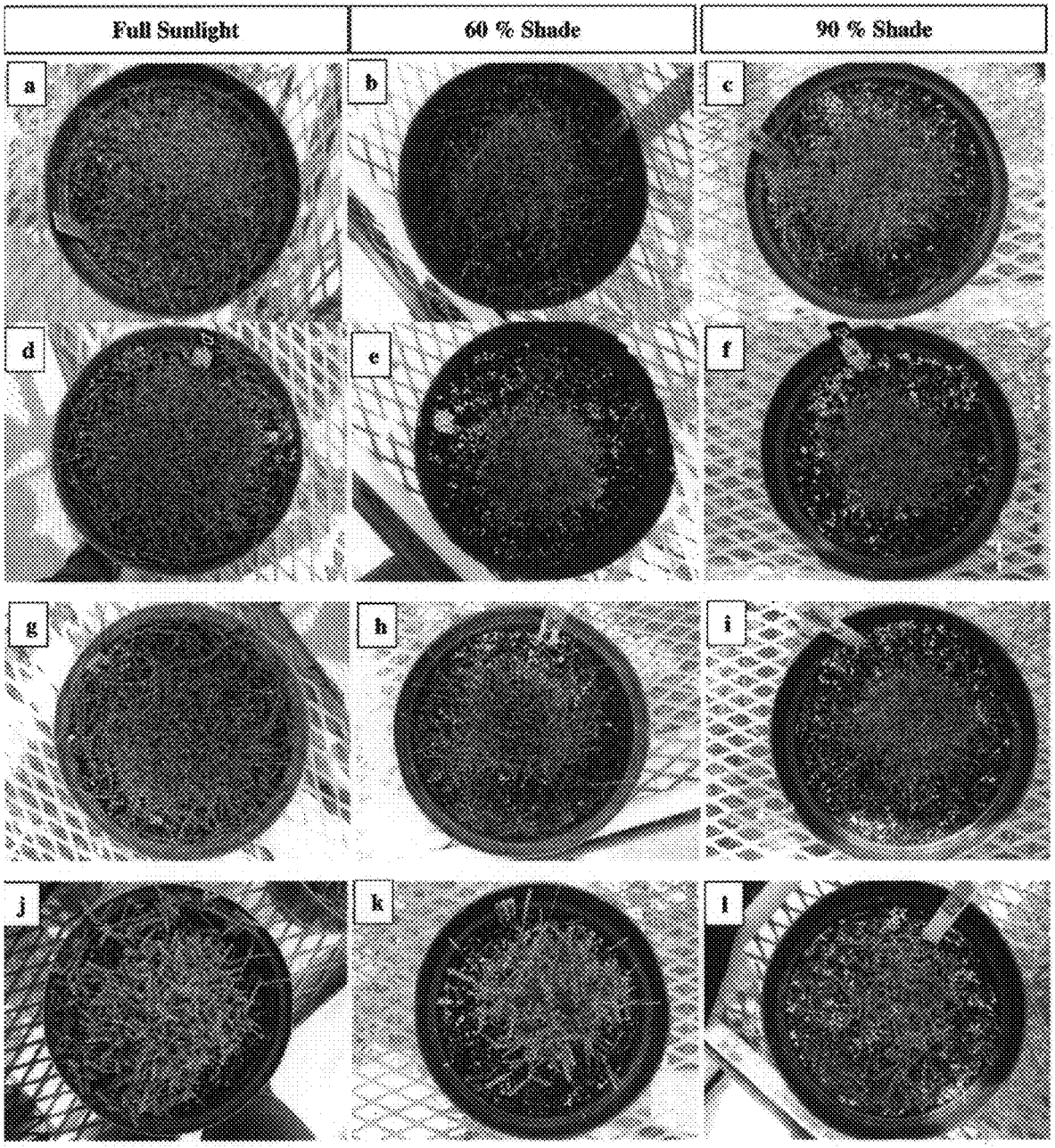
FIG. 4—Shows the percent establishment of 'DALZ 1308' (a, b, c), 'Diamond' (d, e, f), 'Zorro' (g, h, i), and 'Palisades' (j, k, l) under full sunlight, 60% shade, and 90% shade, respectively.

The shade tolerance of 'DALZ 1308', 'Diamond', 'Palisades' (U.S. Plant Pat. No. 11,515), and 'Zorro' (U.S. Plant Pat. No. 14,130) were compared in 2013 and 2014 (Tables 11-13; FIG. 4). For each entry, 9 replicates of 8.9 cm-diameter square plugs were transplanted into 20 cm-diameter round pots filled with Sunshine VP mix. Plant material was acclimated to full sunlight, 60% shade, or 90% shade for two weeks before starting data collection on Aug. 15, 2013 and Jul. 11, 2014. 60% and 90% shade densities were achieved by covering PVC frames of 274 cm L×152 cm W×91 cm H dimensions with 60% and 80% black polypropylene shade cloth to account for filtered light through the glass roofs, respectively. All pots were irrigated uniformly and as-needed to maintain adequate moisture for each shade treatment. Establishment rate in the form of percent green cover was determined by digital image analysis from pictures taken at a height of 40.6 cm at 69 (Oct. 23, 2013) and 68 (Sep. 17, 2014) days after treatment (DAT). Images were processed in SigmaScan Pro Version 5.0 with the Turf Analysis 1.2 macro. Plant height (cm) was measured every two weeks from the three longest uncut leaves in each replicated pot. Growth rates (mm/d) were calculated as follows: [(mean plant height−height of cut)/(number of days since the last mowing event)]×10. This data was collected at 41 (September 25) and 54 (October 8) DAT in 2013, and at 17 (July 28), 33 (August 13), 49 (August 29), and 68 (September 17) DAT in 2014. Pots were trimmed every two weeks at a uniform height of 4.0 cm after collecting measurements. Turfgrass quality, shoot density, and color were visually rated on a "1" to "9" scale (1=brown/dead, bare; 6=minimum quality, medium density and medium green color; 9=excellent quality, very dense, and dark green). Turfgrass quality was rated at 69 (Oct. 23, 2013) and 68 (Sep. 17, 2014) DAT. Shoot density and color were only rated in 2014 at 17, 33, 49, and 68 DAT.

TABLE 2

Visual ratings for 'DALZ 1308' compared to a commercial zoysiagrass cultivar in Gainesville, FL from 2006 to 2008 and 2014 to 2016.

| | 2006-2008 | | | |
|---|---|---|---|---|
| Entry | Turfgrass Quality† | Genetic Color† | Shoot Density† | Spring Greenup‡ |
| | 1 to 9 | | | |
| 'DALZ 1308' | 6.9 a | 7.7 a | 7.5 a | 7.3 a |
| 'Diamond' | 6.0 a | 6.0 b | 6.3 b | 6.5 a |
| LSD‡‡ | 1 | 0.8 | 1.1 | 1 |

| | 2006-2008 | | 2014-2016 | |
|---|---|---|---|---|
| Entry | Seedhead Density§ | Mole Cricket Resistance | Percent Establishment# (%) | Turfgrass Quality†† |
| | 1 to 9 | | | 1 to 9 |
| 'DALZ 1308' | 5.0 a | 9.0 a | 92.1 a | 7.0 a |
| 'Diamond' | 3.3 b | 8.5 a | 85.0 a | 6.9 a |
| LSD‡‡ | 1.4 | 1.2 | 15.2 | 0.4 |

†Means presented for turfgrass quality (1 = low; 9 = excellent), genetic color (1 = brown; 9 = dark green) and shoot density (1 = low; 9 = high) are combined from four collection dates. Cultivar by year was not significant; means were combined.
‡Spring greenup (1 = brown; 9 = completely green) was rated in January and March 2007. Means were not significantly different between dates.
§Seedhead density (1 = high density; 9 = low density) was rated once in January 2007.

TABLE 2-continued

Visual ratings for 'DALZ 1308' compared to a commercial zoysiagrass cultivar in Gainesville, FL from 2006 to 2008 and 2014 to 2016.

¶Mole cricket resistance (1 = completely susceptible; 9 = highly resistant) was rated in August and December 2006. Means were not significantly different between dates.
#Establishment ratings were visually rated in April 2014, ten months after planting in June 2013.
††Turfgrass quality was visually rated monthly on a 1-9 scale (1 = brown/dead; 6 = minimum acceptable; 9 = excellent). Means were determined from ratings collected from during various months in 2014 and 2015 Cultivar by year and cultivar by season were not significant factors. Means were pooled across years and collection dates.
‡‡Cultivars followed by the same letter in each column are not significantly different by Fisher's protected LSD (P > 0.05).

TABLE 3

Percent establishment of 'DALZ 1308' compared to commercial zoysiagrass cultivars.

| | Establishment (%) † | | | | | |
|---|---|---|---|---|---|---|
| | | | Southeast | | | |
| | North Central (IN) | | | Summer | Fall | |
| Entry | Summer | Fall | Spring | | FL | GA |
| 'DALZ 1308' | 12.3 ab | 60.9 a | 64.3 a | 63.2 a | 43.3 a | 73.3 a |
| 'Diamond' | 10.7 b | 63.3 a | 65.8 a | 62.6 a | 43.3 a | 61.1 b |
| 'L1F' | 15.7 a | 80.9 a | 74.0 a | 66.5 a | 41.7 a | 63.3 b |
| LSD‡ | 4.1 | 42.5 | 13.2 | 15.4 | 24.8 | 4.4 |

| | Establishment (%) † | | | | | |
|---|---|---|---|---|---|---|
| | Southeast | | | | | |
| | Fall | | | Transition Zone (KY) | | |
| Entry | MS | TX | Avg. | Spring | Summer | Fall |
| 'DALZ 1308' | 44.2 b | 80.0 b | 60.2 b | 41.7 a | 45.8 a | 31.7 a |
| 'Diamond' | 37.5 b | 86.7 ab | 57.2 b | 18.3 a | 29.2 a | 25.8 a |
| 'L1F' | 77.5 a | 90.0 a | 68.1 a | 33.3 a | 43.8 a | 40.9 a |
| LSD‡ | 21.7 | 6.7 | 5.2 | 32.1 | 29.9 | 43.0 |

†Establishment was rated visually on a percentage scale (0-100%) in 2013 and 2014. Due to unusually harsh winter conditions in 2013, plots were replanted in the spring of 2014 in AR and IN, and in the summer of 2014 in KY (Diamond only). DALZ 1308 and checks were not replanted in VA. Data is presented by season (spring, March-May; summer, June-September; fall, October and November) within regions, and by location if a significant entry by location interaction was present. The north central region only represents Bloomington, IN in the summer and fall of 2014. Southeastern locations included Jay, FL; Griffin, GA; Starkville, MS; and College Station, TX. Spring means are from GA, MS, and TX in 2014. Summer means are from MS and TX in 2013, and GA and TX in 2014. Fall means are from FL, MS, and TX in 2013, and GA in 2014. The transition zone location represented here is KY in fall (2013), spring (2014) and summer (2013 and 2014). Data on establishment was not provided by southwestern locations Tucson, AZ and Rancho Mirage, CA.
‡Entry means were separated using Fisher's Protected LSD. Means followed by the same letter in each column are not significantly different (P >0.05).

TABLE 4

Turfgrass quality of 'DALZ 1308' compared to commercial zoysiagrass cultivars in the southwestern and southeastern regions.

| | Summer Turfgrass Quality† | | | | | | | |
|---|---|---|---|---|---|---|---|---|
| | Southwest | | | | | | Southeast | |
| | AZ | | | | | | | |
| Entry | '14 | '15 | '16 | '17 | CA | Avg. | FL | GA |
| 'DALZ 1308' | 6.3 b | 8.0 a | 7.5 a | 5.4 a | 5.9 a | 6.3 a | 6.3 a | 5.6 a |
| 'Diamond' | 6.7 b | 6.9 a | 6.7 a | 6.6 a | 6.2 a | 6.5 a | 6.6 a | 5.8 a |
| 'L1F' | 7.2 a | 7.1 a | 6.9 a | 6.0 a | 6.3 a | 6.6 a | 6.7 a | 5.7 a |
| LSD‡ | 0.5 | 1.1 | 0.8 | 1.2 | 0.6 | 0.4 | 0.7 | 0.6 |

TABLE 4-continued

Turfgrass quality of 'DALZ 1308' compared to commercial zoysiagrass cultivars in the southwestern and southeastern regions.

| | Summer Turfgrass Quality† | | | | | | |
|---|---|---|---|---|---|---|---|
| | Southeast | | | | | | |
| | | TX | | | | | |
| Entry | MS | '14 | '15 | '16 | '17 | Avg. | Avg. |
| 'DALZ 1308' | 6.4 a | 6.9 a | 8.0 a | 5.7 a | 6.1 a | 6.2 a | 6.3 a |
| 'Diamond' | 5.9 ab | 5.1 b | 7.2 b | 5.5 ab | 5.6 a | 6.0 a | 6.2 a |
| 'L1F' | 5.7 b | 6.9 a | 6.9 b | 4.2 b | 5.8 a | 6.0 a | 6.2 a |
| LSD‡ | 0.6 | 1.6 | 0.7 | 1.4 | 0.9 | 0.3 | 0.2 |

†Turfgrass quality rated on a 1-9 scale (1 = brown/dead; 9 = excellent; 6 = minimum acceptable) was collected monthly from six southern locations (Tucson, AZ; Rancho Mirage, CA; Jay, FL; Griffin, GA; Starkville, MS; and College Station, TX) in two regions (southwest and southeast) from 2014 through 2017.
‡Entry means were separated using Fisher's Protected LSD. Means followed by the same letter in each column are not significantly different (P > 0.05).

TABLE 5

Turfgrass quality for 'DALZ 1308' compared to commercial zoysiagrass cultivars within the north central region and the transition zone.

| | Summer Turfgrass Quality† | | | | | | | | |
|---|---|---|---|---|---|---|---|---|---|
| | North Central | | | Transition Zone VA | | | | | |
| Entry | IN | AR | KY | '14 | '15 | '16 | '17 | Avg. | Avg. |
| 'DALZ 1308' | 7.2 a | 5.8 a | 6.9 a | 4.7 b | 5.9 a | 6.5 a | 6.5 a | 6.4 a | 6.6 a |
| 'Diamond' | 6.1 b | 5.7 a | 6.0 b | 3.7 b | 4.6 a | 5.7 a | 5.8 ab | 5.6 b | 5.8 b |
| 'L1F' | 4.0 c | 6.5 a | 5.9 b | 6.4 a | 5.9 a | 5.6 a | 4.5 b | 6.1 ab | 5.6 b |
| LSD‡ | 0.7 | 1.3 | 0.7 | 1.4 | 1.5 | 1.9 | 1.5 | 0.5 | 0.4 |

†Turfgrass quality rated on a 1-9 scale (1 = brown/dead; 9 = excellent; 6 = minimum acceptable) was collected monthly from four northern locations (Fayetteville, AR; Bloomington, IN; Lexington, KY; and Richmond, VA) in two regions (north central and transition zone) from 2014 through 2017.
‡Entry means were separated using Fisher's Protected LSD. Means followed by the same letter in each column are not significantly different (P > 0.05).

TABLE 6

Additional traits of 'DALZ 1308' compared to commercial zoysiagrass cultivars in the 2013 NTEP evaluation.

| | Leaf | Genetic | Seasonal Color§ | | | |
|---|---|---|---|---|---|---|
| Entry | Texture† | Color‡ | Summer 1 to 9 | Fall | Winter | Avg |
| 'DALZ 1308' | 7.5a | 6.8a | 5.4a | 6.9a | 6.0a | 6.5a |
| 'Diamond' | 6.8b | 6.6a | 6.0a | 6.2a | 5.8a | 6.1a |
| 'L1F' | 6.2c | 6.5a | 6.1a | 6.4a | 5.7a | 6.1a |
| LSD‡ | 0.4 | 0.3 | 2.2 | 0.7 | 1.6 | 0.5 |

| | Shoot Density¶ | | | | Seedhead | Spring |
|---|---|---|---|---|---|---|
| Entry | Spring | Summer | Fall | Avg 1 to 9 | Density# | Greenup†† |
| 'DALZ 1308' | 6.9a | 7.2a | 7.4a | 7.3a | 5.5a | 6.2a |
| 'Diamond' | 7.0a | 6.9a | 6.7b | 6.9b | 6.3a | 6.2a |
| 'L1F' | 6.2h | 6.9a | 6.9b | 6.8b | 5.9a | 5.9a |
| LSD‡ | 0.5 | 0.5 | 0.4 | 0.3 | 3.6 | 1.0 |

†Leaf texture was visually rated once each growing season on a 1-9 scale (1 = very coarse; 9 = very fine) in AZ (2014-2017), CA (2014, 2015 and 2017), IN (2014 and 2016), MS (2014-2017), and TX (2014-2017).
‡Genetic color was visually rated on a 1-9 scale (1 = brown; 9 = dark green) once during the growing season of 2014 (IN, KY, VA) and of 2015 (AR). Data was collected from 2014 through 2017 in each AZ, CA, FL, GA, MS, and TX.

TABLE 6-continued

Additional traits of 'DALZ 1308' compared to commercial zoysiagrass cultivars in the 2013 NTEP evaluation.

§Seasonal color was rated on a 1-9 scale (1 = brown; 9 = dark green) during the summer, fall, and winter. Late summer ratings included those from FL and GA in 2014 and 2015. Fall color is represented by ratings from AR (2014 and 2015), AZ (2014, 2015, and 2017), FL (2013-2017), GA (2014-2017), IN (2014 and 2015), KY (2015), MS (2013-2017), TX (2014 and 2015), and VA (2014-2016). Winter color ratings were collected in AZ (2014-2017), CA (2016 and 2017), MS (2013-2016), and TX (2015-2017).
¶Shoot density was visually rated on a 1-9 scale (1 = very sparse; 9 = very dense) during the spring, summer, and fall. Spring ratings were collected in AZ (2017), CA (2015), MS (2014-2017), and FL (2015-2017). Summer density was collected in AZ (2017), CA (2015), FL (2014-2017), MS (2014-2017), and TX (2014 and 2015). Fall density ratings were collected in AZ (2014, 2016, and 2017), CA (2015), FL (2014-2017), MS (2014-2017), and TX (2014 and 2015).
#Seedhead density was rated on a 1-9 scale (1 = very dense; 9 = no seedheads) in FL, IN, TX, and VA in 2015, in IN in 2016, and in AZ and FL in 2017.
††Spring greenup was visually rated on a 1-9 scale (1 = no living tissue; 9 = completely green) in CA (2014 and 2015), VA (2014), AZ and TX (2016 and 2017), and from 2014-2017 in FL, GA, IN, KY and MS.
‡‡Entry means were separated using Fisher's Protected LSD. Means followed by the same letter in each column are not significantly different (P > 0.05)

TABLE 7

Percent winterkill and seasonal living cover of 'DALZ 1308' compared to commercial zoysiagrass cultivars.

| | Winter | Living Cover‡ | | | | | | |
|---|---|---|---|---|---|---|---|---|
| | kill | Spring | | | | | | |
| Entry | (IN)† | AZ | CA | GA | IN | KY | VA | Avg. |
| | | % | | | | | | |
| 'DALZ 1308' | 28.3a | 93.0a | 82.4a | 86.3a | 93.2a | 78.3a | 81.7a | 85.8a |
| 'Diamond' | 56.7b | 98.7a | 92.9a | 86.7a | 89.5ab | 53.3a | 75.0a | 82.7a |
| 'L1F' | 97.3c | 91.0a | 92.5a | 83.3a | 42.5b | 75.0a | 94.7a | 79.8a |
| LSD§ | 28.2 | 17.6 | 19.6 | 14.8 | 50.3 | 65.2 | 29.8 | 9.9 |

| | Living Cover‡ | | | | | | | |
|---|---|---|---|---|---|---|---|---|
| | Summer | | | | | Fall | | |
| Entry | AZ | CA | IN | VA | Avg. | AZ | CA | Avg. |
| | % | | | | | | | |
| 'DALZ 1308' | 96.5b | 71.7b | 79.0a | 91.5a | 84.7a | 96.7a | 75.3a | 86.0a |
| 'Diamond' | 98.9a | 86.7a | 51.7a | 84.2a | 80.4ab | 98.3a | 72.0a | 85.2a |
| 'L1F' | 99.0a | 89.7a | 6.0b | 98.4a | 73.3b | 98.7a | 64.4a | 81.5a |
| LSD§ | 0.6 | 14.4 | 27.4 | 23.2 | 7.3 | 40.1 | 124.7 | 101.8 |

†Winterkill was visually rated as a percentage of dead tissue after spring greenup in Bloomington, IN in 2014. Means are presented as they appear in the 2014 NTEP report.
‡Living cover was rated in the spring, summer, and fall as a percentage of living tissue. Spring ratings reflect AZ (2015-2017), CA (2014, 2016, and 2017), GA (2015), IN (2015 and 2017), KY (2015), and VA (2014). Summer ratings were collected for AZ (2014 and 2017), CA (2014), IN (2014), and VA (2014). Fall ratings were only collected in AZ (2017) and CA (2014 and 2015).
§Entry means were separated using Fisher's Protected LSD at P < 0.05. Means followed by the same letter in each column are not significantly different.

TABLE 8

Ball roll distance (cm) of 'DALZ 1308' compared to commercial zoysiagrass cultivars measured in NTEP locations and Dallas, TX.

| | NTEP† | | | |
|---|---|---|---|---|
| Entry | AZ | CA | FL | KY |
| 'DALZ 1308' | 174.5 a | 123.2 a | 188.7 a | 137.7 a |
| 'Diamond' | 158.8 b | 121.9 a | 175.5 a | 120.7 b |
| 'L1F' | 153.9 b | 121.7 a | 167.1 a | 122.2 b |
| LSD§ | 14.5 | 8.4 | 27.4 | 11.9 |

| | NTEP† | | | |
|---|---|---|---|---|
| Entry | MS | VA | Avg. | TX‡ |
| 'DALZ 1308' | 196.1 a | 168.1 a | 165.1 a | 229.6 a |
| 'Diamond' | 192.3 a | 181.4 a | 158.2 a | 218.7 b |

TABLE 8-continued

Ball roll distance (cm) of 'DALZ 1308' compared to commercial zoysiagrass cultivars measured in NTEP locations and Dallas, TX.

| | | | | |
|---|---|---|---|---|
| 'L1F' | 191.3 a | 183.4 a | 156.0 a | 198.9 c |
| LSD§ | 20.3 | 27.7 | 17.8 | 9.9 |

†Ball roll was measured repeatedly between May and December from 2014 through 2017 in AZ, CA, FL, KY, and MS. Data from VA was collected from 2014 through 2016.
‡Ball roll was measured and calculated according to Brede (1990) in 2017 on 15 Aug., 16 Aug., 28 Aug., 29 Aug., 6 Sep., 7 Sep., 13 Sep., and 14 Sep. Analysis of variance determined entry by date was not significant, so means were pooled.
§Entry means were separated using Fisher's Protected LSD at $P < 0.05$. Means followed by the same letter in each column are not significantly different.

TABLE 9

Characteristics of 'DALZ 1308' compared to commercial zoysiagrass cultivars in Dallas, TX from 2014 through 2017.

| Entry | Establishment† | | | Turfgrass Quality‡ | | |
|---|---|---|---|---|---|---|
| | May | June | July | | | |
| | 2015 | 2015 | 2015 | Spring | Summer | Fall |
| 'DALZ 1308' | 36.7 b | 40.0 b | 55.0 c | 6.0 a* | 6.6 a | 5.0 ab |
| 'Diamond' | 58.3 a | 51.7 a | 61.7 b | 4.7 a | 5.5 b | 4.2 b |
| 'L1F' | 51.7 a | 60.0 a | 75.0 a | 5.3 a | 5.3 b | 5.5 a |
| LSD‡‡ | 13.6 | 8.9 | 3.8 | 2.4 | 0.6 | 1.1 |

| Entry | Shoot Density§ | Genetic Color¶ | Fall Color# | Spring Greenup†† |
|---|---|---|---|---|
| 'DALZ 1308' | 6.2 a | 6.1 a | 4.7 a | 4.0 a |
| 'Diamond' | 5.5 a | 6.4 a | 3.7 a | 3.0 a |
| 'L1F' | 6.3 a | 5.4 b | 4.7 a | 4.0 a |
| LSD‡‡ | 1.1 | 0.5 | 1.1 | 2.3 |

†This trial was planted with three replications on 4 Sep. and 5 Sep. 2014. Establishment was visually rated in the summer of 2015 from 1 to 100% cover. A significant entry by date interaction was observed, so data are presented for each collection date.
‡Turfgrass quality means rated 1 to 9 (1 = brown/dead; 9 = excellent; 6 = minimum acceptable) are presented by season. Spring means occurred once on 31 May 2017. Summer ratings occurred from July through September in 2016, and from July through September in 2017. Fall ratings occurred in October 2015 and November 2016.
§Shoot density was rated from 1 to 9 (1 = very sparse; 9 = very dense) in April 2016 and September 2017.
¶Genetic color was rated from 1 to 9 (1 = brown; 9 = dark green) in July and September 2015, April and August 2016, and June 2017.
#Fall color was rated from 1 to 9 (1 = brown; 9 = dark green) in November 2015 and 2016.
††Spring greenup was rated from 1 to 9 (1 = brown; 9 = completely green) in early March 2017.
‡‡Entries followed by the same letter in each column are not significantly different ($P > 0.05$) by Fisher's protected LSD

TABLE 10

Percent seedheads of 'DALZ 1308' compared to commercial zoysiagrass cultivarsvisually rated in Dallas, TX from 2015 to 2017.

| Entry | Seedheads† | | | | | | |
|---|---|---|---|---|---|---|---|
| | Spring | | Summer | | | Fall | |
| | May 2015 | April 2017 | June 2016 | September 2016 | September 2017 | October 2015 | November 2016 |
| | % | | | | | | |
| 'DALZ 1308' | 0.0 b | 100.0 a | 0.0 c | 2.3 c | 8.3 b | 1.7 c | 1.7 b |
| 'Diamond' | 35.0 a | 80.0 a | 66.7 b | 91.7 a | 60.0 a | 90.0 a | 100.0 a |
| 'L1F' | 23.3 ab | 15.0 b | 88.3 a | 61.7 b | 10.0 b | 45.0 b | 41.7 b |
| LSD‡ | 32.6 | 23.6 | 16.7 | 20.7 | 3.8 | 32.9 | 42.8 |

†Seedheads were visually rated from 1 to 100%. Means are presented by collection date. Spring ratings occurred in May 2015 and April 2017. Summer ratings occurred in June 2016 and in September 2016 and 2017. Fall ratings occurred in October 2015 and November 2016.
‡Entries followed by the same letter in each column are not significantly different ($P > 0.05$) by Fisher's protected LSD.

TABLE 11

Percent green cover, turfgrass quality, and color ratings of 'DALZ 1308' compared to commercial zoysiagrass cultivars measured in a greenhouse under full sun, 60% shade, and 90% shade.

| Trait | Entry | Shade Levels | | | |
|---|---|---|---|---|---|
| | | Full Sun | 60% | | 90% |
| Green Cover (%)† | 'DALZ 1308' | 91.0 a | 46.1 a | | 22.4 a |
| | 'Diamond' | 69.4 b | 32.3 b | | 17.6 a |
| | 'Palisades' | 83.1 a | 23.2 b | | 5.8 b |
| | 'Zorro' | 85.7 a | 27.2 b | | 15.9 a |
| | LSD¶ | 13.0 | 10.9 | | 9.0 |
| Turfgrass | | | 2013 | 2014 | |
| Quality‡ | 'DALZ 1308' | 8.8 a | 7.7 a | 6.3 a | 4.2 a |
| | 'Diamond' | 8.0 b | 6.3 a | 6.7 a | 4.3 a |
| | 'Palisades' | 7.8 b | 3.3 b | 7.0 a | 3.8 a |
| | 'Zorro' | 8.2 b | 5.3 ab | 7.3 a | 3.8 a |
| | LSD¶ | 0.5 | 2.8 | 1.4 | 0.9 |
| Turfgrass Colors§ | 'DALZ 1308' | 8.1 a | 7.8 a | | 7.3 b |
| | 'Diamond' | 8.2 a | 7.8 a | | 7.9 a |
| | 'Palisades' | 7.5 b | 8.0 a | | 7.6 ab |
| | 'Zorro' | 8.0 ab | 7.8 a | | 7.8 a |
| | LSD¶ | 0.6 | 0.3 | | 0.4 |

†After 69 (23 Oct. 2013) and 68 (17 Sep. 2014) DAT, establishment rates in the form of percent green cover were determined by digital image analysis.
‡Turfgrass quality ratings were visually rated on a 1-9 scale (1 = brown/dead; 6 = minimum acceptable; 9 = excellent) at 69 (23 Oct. 2013) and 68 (17 Sep. 2014) DAT. The lower significant ratings observed under 60% shade in 2013 can be attributed to different trial end dates (23 Oct. 2013 and 17 Sep. 2014) and shorter daylengths indicative of sub-optimum growing conditions.
§Turfgrass color was rated on a 1-9 scale (1 = brown/dead; 6 = medium green; 9 = dark green) at 17 (7/28), 33 (8/13), 49 (8/29), and 68 (9/17) DAT in 2014.
Fisher's protected LSD was used to determine significant differences. Means followed by the same letter in each column are not significantly different ($P > 0.05$).

TABLE 12

Growth rates (mm/d) of 'DALZ 1308' compared to commercial zoysiagrass cultivars under full sun, 60% shade, and 90% shade.

| Entry | Shade Levels† | | | | | | |
|---|---|---|---|---|---|---|---|
| | Full Sun | 60% Shade | | | | | |
| | | 2013 | | 2014 | | | |
| | 2013-2014 | 41 | 54 | 17 | 33 | 49 | 68 |
| | $mm \cdot d^{-1}$ | | | | | | |
| 'DALZ 1308' | 1.0 c | 2.6 bc | 1.2 b | 2.4 c | 3.6 b | 3.4 c | 2.3 c |
| 'Diamond' | 0.8 c | 2.1 c | 0.6 b | 2.6 bc | 2.8 b | 3.7 c | 2.7 c |
| 'Palisades' | 3.5 a | 8.0 a | 2.3 a | 8.0 a | 7.3 a | 11.3 a | 8.9 a |
| 'Zorro' | 2.7 b | 3.7 b | 1.1 b | 3.5 b | 3.5 b | 5.4 b | 4.2 b |
| LSD‡ | 0.5 | 1.4 | 0.8 | 1.0 | 1.5 | 1.4 | 0.7 |

| Entry | Shade Levels† | | | | |
|---|---|---|---|---|---|
| | 90% Shade | | | | |
| | | 2014 | | | |
| | 2013 | 17 | 33 | 49 | 68 |
| | $mm \cdot d^{-1}$ | | | | |
| 'DALZ 1308' | 1.0 a | 1.9 c | 2.6 b | 3.1 b | 2.8 b |
| 'Diamond' | 0.7 a | 1.9 c | 2.1 b | 3.1 b | 2.2 b |
| 'Palisades' | 0.4 a | 6.2 a | 7.7 a | 8.3 a | 6.1 a |
| 'Zorro' | 1.1 a | 2.7 b | 2.1 b | 2.9 b | 3.1 b |
| LSD‡ | 0.7 | 0.6 | 1.6 | 0.9 | 1.8 |

†Growth rates were calculated in millimeters per day at 41 (9/25) and 54 (10/8) DAT in 2013 and at 17 (7/28), 33 (8/13), 49 (8/29), and 68 (9/17) DAT in 2014. Pots were trimmed every two weeks at a uniform height of 4.0 cm after collecting measurements.
‡Fisher's protected LSD was used to determine significant differences. Means followed by the same letter in each column are not significantly different ($P > 0.05$).

TABLE 13

Shoot density ratings of 'DALZ 1308 'compared to commercial zoysiagrass cultivars under full sun, 60 % shade, and 90% shade.

| | Shade Levels† | | | |
|---|---|---|---|---|
| | Full Sun | | | |
| Entry | 17 | 33 | 49 | 68 |
| | 1 to 9 | | | |
| 'DALZ 1308' | 9.0 a | 9.0 | 9.0 | 9.0 |
| 'Diamond' | 9.0 a | 9.0 | 9.0 | 9.0 |
| 'Palisades' | 8.3 b | 8.0 | 9.0 | 9.0 |
| 'Zorro' | 8.0 b | 8.0 | 9.0 | 8.0 |
| LSD‡ | 0.6 | N/A | N/A | N/A |

| | Shade Levels† | | | | |
|---|---|---|---|---|---|
| | 60% Shade | | | | |
| Entry | 17 | 33 | 49 | 68 | 90% Shade |
| | 1 to 9 | | | | |
| 'DALZ 1308' | 7.7 b | 7.0 b | 5.7 b | 7.3 a | 6.8 b |
| 'Diamond' | 8.5 a | 8.0 a | 7.0 a | 6.7 a | 7.9 a |
| 'Palisades' | 8.0 ab | 8.0 a | 7.0 a | 6.7 a | 5.8 c |
| 'Zorro' | 8.0 ab | 6.0 c | 8.0 a | 8.0 a | 6.9 b |
| LSD‡ | 0.6 | 1.0 | 1.2 | 1.8 | 0.7 |

†Shoot density was rated on a 1-9 scale (1 = very sparse; 6 = moderately dense; 9 = very dense) at 17 (7/28), 33 (8/13), 49 (8/29), and 68 (9/17) DAT in 2014.
‡Fisher's protected LSD was used to determine significant differences. Means followed by the same letter in each column are not significantly different (P > 0.05). An "N/A" is indicated for DAT where no variation in data was observed.

Traits and Characteristics of 'DALZ 1308'

Establishment: 'DALZ 1308' establishment was similar to 'Diamond' in IN, FL, MS, TX, and KY. 'DALZ 1308' establishment was similar to 'L1F' in IN, FL, and KY. 'L1F' establishment was superior to 'DALZ 1308' in TX and MS. 'DALZ 1308' establishment was superior to 'Diamond' and 'L1F' in GA. (Table 3).

Turf quality: 'DALZ 1308' turf quality was similar to 'Diamond' and 'L1F' in the southwest region, except in AZ for year 2014, where 'L1F' had superior turfgrass quality compared to 'DALZ 1308'. 'DALZ 1308' turf quality was similar to 'Diamond' and 'L1F' in FL and GA. 'DALZ 1308' turfgrass quality was superior to 'L1F' in MS. 'DALZ 1308' turf quality was similar to or superior to 'Diamond' and 'L1F' in Texas (Table 4). 'DALZ 1308' turf quality was superior to that of 'Diamond' and 'L1F' in the northern central region. 'DALZ 1308' turf quality was similar to or superior to 'Diamond' and 'L1F' across the transition zone (AR, KY, and VA) (Table 5).

Leaf texture: 'DALZ 1308' leaf texture was significantly finer than that of 'Diamond' and 'L1F' (Table 6).

Genetic color: 'DALZ 1308' genetic color was similar to 'Diamond' and 'L1F' across all locations.

Spring green-up: 'DALZ 1308' spring green-up was similar to 'Diamond' and 'L1F' across most locations, except in VA, where 'L1F' green-up was superior to 'DALZ 1308' and in CA, where 'Diamond' and 'L1F' green-up was superior to 'DALZ 1308' (2015 NTEP report).

Percent winterkill: 'DALZ 1308' had a lower winterkill (28%) as compared to 'Diamond' (57%) and 'L1F' (97%) in IN (Table 7).

Fall color retention: 'DALZ 1308' fall color was superior to 'Diamond' and 'L1F' in Dallas, Tex. Fall color retention is a desirable trait extending the green appearance of the turf stand into the autumn season. Improved fall color retention in 'DALZ 1308' in Dallas, Tex. was not observed to be associated with increased winter injury compared to 'Diamond' and 'L1F' (data not shown).

Ball roll distance: 'DALZ 1308' ball roll distance was similar to 'Diamond' and 'L1F' in most locations, except for AZ, KY, and TX where 'DALZ 1308' ball roll distance was superior to 'Diamond' and 'L1F' (Table 8).

Seedhead density during peak growing season: 'DALZ 1308' seedhead density is significantly reduced during peak growing season compared to 'Diamond' and 'L1F' in TX (Table 10). Reduced seed head density would likely result in reduced need for the use of plant growth regulators for fall seedhead suppression.

Establishment—shade response: 'DALZ 1308' establishment under 60% shade was superior to that of 'Diamond', 'Palisades', and 'Zorro' (Table 11).

What is claimed is:

1. A new and distinct interspecific hybrid variety of zoysiagrass named 'DALZ 1308' as shown and described herein.

* * * * *